(12) United States Patent
Davis

(10) Patent No.: US 10,296,529 B2
(45) Date of Patent: May 21, 2019

(54) AUTOMATED ADVANCED RESUSCITATION TRAINING GENERATION SYSTEM AND METHOD THEREFOR

(71) Applicant: The Regents of the University of California, Oakland, CA (US)

(72) Inventor: Daniel P. Davis, Cardiff, CA (US)

(73) Assignee: The Regents of the University of California, Oakland, CA (US)

( * ) Notice: Subject to any disclaimer, the term of this patent is extended or adjusted under 35 U.S.C. 154(b) by 453 days.

(21) Appl. No.: 14/427,439

(22) PCT Filed: Sep. 13, 2013

(86) PCT No.: PCT/US2013/059624
§ 371 (c)(1),
(2) Date: Mar. 11, 2015

(87) PCT Pub. No.: WO2014/043449
PCT Pub. Date: Mar. 20, 2014

(65) Prior Publication Data
US 2015/0242498 A1    Aug. 27, 2015

Related U.S. Application Data

(60) Provisional application No. 61/700,745, filed on Sep. 13, 2012.

(51) Int. Cl.
*G06F 16/35* (2019.01)
*G06F 16/33* (2019.01)
(Continued)

(52) U.S. Cl.
CPC .......... *G06F 16/35* (2019.01); *G06F 16/3331* (2019.01); *G06F 19/325* (2013.01); *G09B 5/00* (2013.01); *G09B 19/003* (2013.01)

(58) Field of Classification Search
CPC ......... G06F 17/30705; G06F 17/30657; G06F 19/325; G09B 5/00
(Continued)

(56) References Cited

U.S. PATENT DOCUMENTS 7,260,480 B1    8/2007  Brown et al.
2008/0171311 A1  7/2008  Center
(Continued)

FOREIGN PATENT DOCUMENTS

| KR | 1020090027084 A | 3/2009 |
| WO | 1994/18657 A1 | 8/1994 |
| WO | 2014043449 A1 | 3/2014 |

OTHER PUBLICATIONS

PCT/US2013/059624 International Search Report and Written Opinion dated Dec. 24, 2013.
EP13836728.9 Extended European Search Report dated May 25, 2016.

*Primary Examiner* — Robert P Bullington
(74) *Attorney, Agent, or Firm* — Wagenknecht IP Law Group, PC

(57) ABSTRACT

A resuscitation training program generation system and method are provided. The system includes an acquisition section that acquires resuscitation event data on a cardiac arrest of a patient; an event categorization section that acquires a categorization of the cardiac arrest into one or more categories of a taxonomy of etiologies of cardiac arrest; an afferent data generator that generates afferent data based on afferent pathways associated with the one or more categories, and updates the resuscitation event data with the generated afferent data; and an efferent data generator that generates a training program for each of the one or more categories based on efferent pathways corresponding to the category and training materials corresponding to the category.

15 Claims, 17 Drawing Sheets

(51) Int. Cl.
*G06F 19/00* (2018.01)
*G09B 5/00* (2006.01)
*G09B 19/00* (2006.01)

(58) Field of Classification Search
USPC .......................................................... 434/365
See application file for complete search history.

(56) References Cited

U.S. PATENT DOCUMENTS

| | | |
|---|---|---|
| 2009/0125333 A1 | 5/2009 | Heywood et al. |
| 2010/0174558 A1 | 7/2010 | Smith et al. |
| 2010/0211127 A1 | 8/2010 | Eerden |
| 2012/0064497 A1* | 3/2012 | Wu ..................... G09B 23/30 434/265 |

* cited by examiner

| Afferents |
|---|
| 1 • Demographics |
| 2 • Antecedent events |
| 3 • Intra-arrest |
| 4 • Post-arrest |
| 5 • Process issues |
| 6 • Clinical interpretation |

FIG. 11A

Demographics

| Core | Supplemental |
|---|---|
| • Age | • Admission diagnosis |
| • Gender | • Comorbidities |
| • Location | • Date of admission |
| • Service | • Hospital day of arrest |
| • Date/time | |

FIG. 11B

| Antecedent Data |
|---|
| • Target preventability |
| • Based on Matrix |
|   • Ventilation |
|   • Perfusion |
|   • Dysrhythmias |
|   • Neurological |
| • Monitor downloads |

FIG. 11C

Intra-arrest

| Core | Supplemental |
|---|---|
| • Bystander CPR | • CPR Process |
| • Defibrillations | • Rate, depth, CCF |
| • Medications | • Pre-/post-shock pauses |
| • Intubation | • Perfusion checks |
| | • Intubation pauses |
| | • Defibrillation accuracy |

FIG. 11D

| CPR Process Metrics | |
|---|---|
| • Chest compression fraction | 91% |
| • Compression rate | 123/min |
| • Compression depth | 2.6 inches |
| • Pre-shock pause | 2.6 sec |
| • Post-shock pause | 3.6 sec |
| • Perfusion check | 4.3 sec |
| • Ventilation rate | 9.7/min |
| • PetCO2 | 15.3 mmHg |

FIG. 11E

| Post-Arrest |
|---|
| • Temperature management |
|   • Supportive critical care |
|   • Emergent PCI |
|   • Neurocritical care |
|     • EEG |
|     • Cerebral edema |
|     • Other monitoring |

FIG. 11F

Process Issues

- Code leadership
- Communication
- Skills performance
- Communication
  - Telecommunications vs. providers
- Medications
- Equipment

FIG. 11G

Clinical

- ART Matrix determination
- Interpretation of process issues
  - Immediate feedback to providers
  - Feedback to leadership
  - Feedback to risk management
- Track-and-trend issues
- Clinical metrics

FIG. 11H

Data Analysis

- Event incidence
  - RRTs per 1,000 discharges
  - Arrests per 1,000 discharges
  - RRT vs. arrest
- Outcomes
  - Survival (event, discharge, neurologic)
  - Hospital mortality
- Unit-specific, service-specific, Matrix-Specific

FIG. 12A

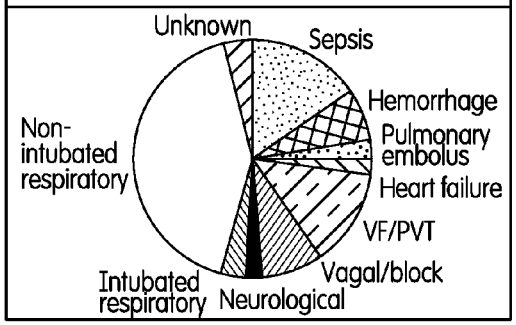

FIG. 12B

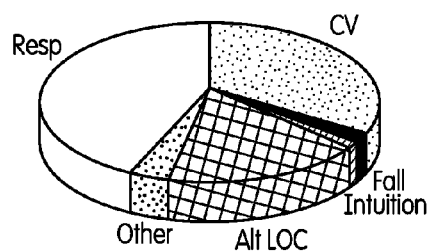

FIG. 12C

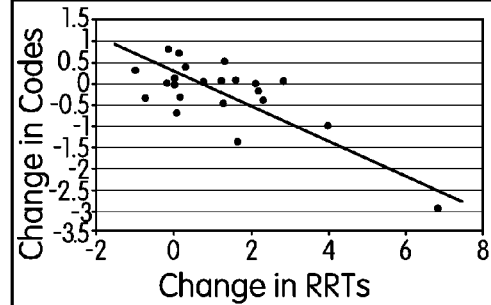

FIG. 12D

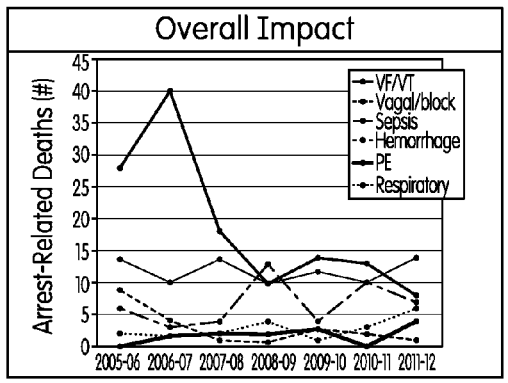
FIG. 12K
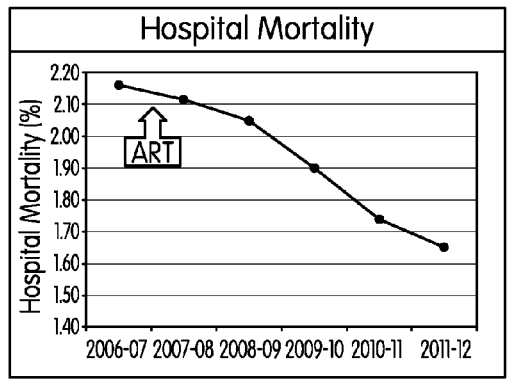
FIG. 12L
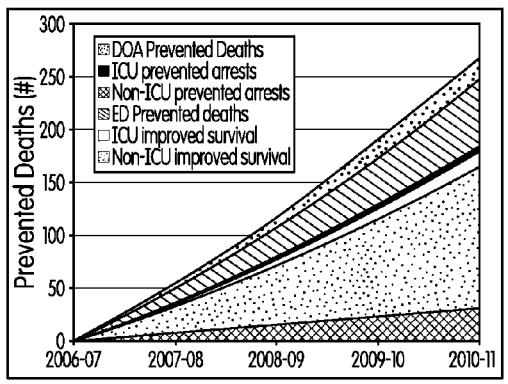
FIG. 12M
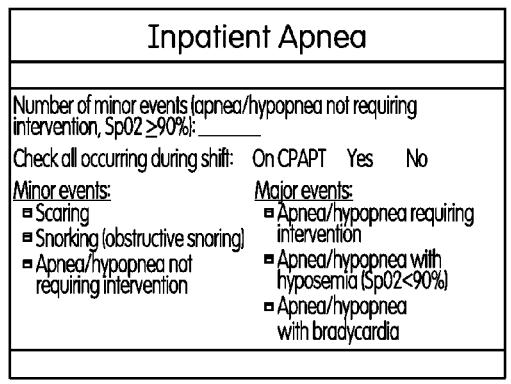
FIG. 12N
FIG. 12O
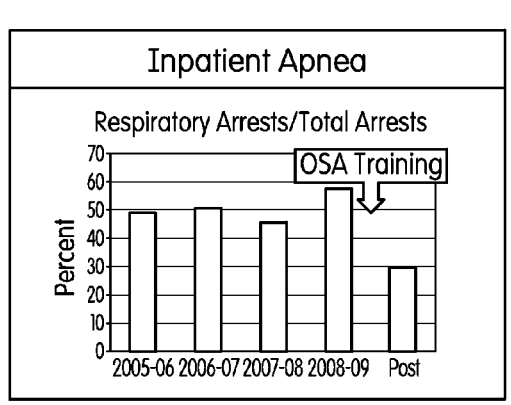
FIG. 13A

AUTOMATED ADVANCED RESUSCITATION TRAINING GENERATION SYSTEM AND METHOD THEREFOR

CROSS-REFERENCE TO RELATED APPLICATIONS

This application is a 35 U.S.C. § 371 National Stage of International Application No. PCT/US2013/059624 filed Sep. 13, 2013, and claims the benefit of priority from U.S. Ser. No. 61/700,745, filed Sep. 13, 2012 in the United States Patent and Trademark Office, the content of each of which is hereby incorporated herein by reference in their entirety for all purposes.

BACKGROUND

1. Field

Methods, devices, systems and articles of manufacture consistent with this disclosure relate to automated advanced resuscitation training generation system and a method therefor.

2. Description of Related Art

Each year, patients have cardiac arrests that require various providers such as doctors, nurses, emergency responders, and the like to perform resuscitation in order to prevent the patient from a fatal arrest. However, with respect to a given individual responder, such resuscitation events are relatively infrequent. For example, a given individual provider may participate in only a few events per year. Accordingly, it can be difficult to formulate resuscitation training for providers in a manner that will influence the outcome of resuscitation events. On the other hand, resuscitation performance is strongly linked to patient outcomes, i.e., whether the patient will live or die, and what quality of life the patient may experience post-arrest. Thus, it is advantageous to provide optimal training and effective pre- and post-arrest treatment algorithms to individual providers.

Related art resuscitation training is derived from generic courses and materials offered by various professional societies, for example, the American Heart Association (AHA), the American College of Surgeons, the American Academy of Pediatrics, etc. Examples of such training programs are an Advanced Cardiac Life Support (ACLS) course, a Basic Life Support (BLS) course, a Pediatric Advanced Life Support (PALS) course, and an Advanced Trauma Life Support (ATLS) course, etc.

Courses such as ACLS and BLS have become quite common, being used, for example, by 97% of hospitals. However, these courses suffer from a common deficiency, namely they are deliberately rigid and standardized, and thus present a "one-sized fits all" approach to resuscitation training. Moreover, while individual hospitals perform in-hospital training according to ACLS and BLS materials and usually provide some form of tracking of this training for individual providers within the hospital, typically the tracking is performed using only a simple spreadsheet for the particular hospital.

SUMMARY

According to an aspect of an exemplary embodiment, there is provided a resuscitation training program generation system comprising at least one microprocessor configured to execute: an acquisition section that acquires resuscitation event data on a cardiac arrest of a patient, from a resuscitation event data storage; an event categorization section that reads matrix data from a matrix data storage that comprises a taxonomy of etiologies of resuscitation, and acquires a categorization of the cardiac arrest into one or more categories of the taxonomy based on the read matrix data; an afferent data generator that reads, for each of the one or more categories, afferent pathways corresponding to the category, generates afferent data based on the afferent pathways, and updates the resuscitation event data with the generated afferent data; and an efferent data generator that, for each of the one or more categories, reads efferent pathways corresponding to the category, from an efferent category storage, and training materials corresponding to the category, from a training materials storage, and generates a training program based on the read efferent pathways and the read training materials.

According to another aspect of one or more exemplary embodiments, there is provided a method of generating a resuscitation training program, the method comprising providing, using at least one microprocessor, a plurality of afferent pathways and efferent pathways to make up a resuscitation training continuous quality improvement (CQI) matrix; hierarchically categorizing, using at least one microprocessor, resuscitation events into one or more hierarchical categories within the CQI matrix; and linking categories of the CQI matrix with at least one of training materials, treatment algorithms, and special initiatives programs to generate the resuscitation training program According to another aspect of one or more exemplary embodiments, there is provided a resuscitation training program generation system comprising acquisition means for acquiring resuscitation event data on a cardiac arrest of a patient; event categorization means for acquiring a categorization of the cardiac arrest into one or more categories of a taxonomy of etiologies of cardiac arrest; afferent data generating means for generating afferent data based on afferent pathways associated with the one or more categories, and for updating the resuscitation event data with the generated afferent data; and efferent data generating means for generating a training program for each of the one or more categories based on efferent pathways corresponding to the category and training materials corresponding to the category.

BRIEF DESCRIPTION OF THE DRAWINGS

The above and other aspects will become apparent from the following description with reference to the following drawings, wherein like reference numerals refer to like parts throughout the various figures unless otherwise specified, and wherein:

FIGS. 11A-11H illustrate examples of the types of afferent data that may be collected for a given category;

FIGS. 13A-13D illustrate examples of new project or initiatives;

DETAILED DESCRIPTION

Figure 1:
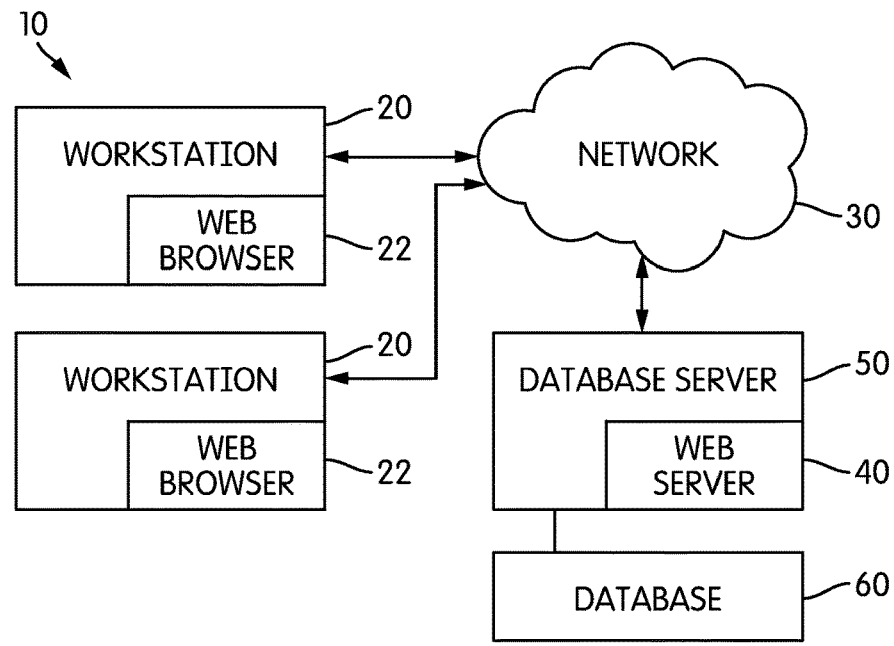
FIG. 1 is a block diagram illustrating an example of a configuration of a medical institution according to an exemplary embodiment.

Exemplary embodiments will be described in detail with reference to the accompanying drawings. The inventive concept, however, may be embodied in various different forms, and should not be construed as being limited only to the illustrated exemplary embodiments. Rather, these exemplary embodiments are provided as examples so that this disclosure will fully convey the inventive concept to those skilled in the art. Accordingly, known processes, elements, and techniques are not described with respect to some of the exemplary embodiments of the inventive concept. Unless otherwise noted, like reference numerals denote like elements throughout the attached drawings and written description, and thus descriptions will not be repeated. In the drawings, the sizes and relative sizes of layers and regions may be exaggerated for clarity.

The terminology used herein is for the purpose of describing particular exemplary embodiments only and is not intended to be limiting of the inventive concept. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Also, the term "exemplary" is intended to refer to an example or illustration.

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and/or the present specification.

FIG. 1 is a block diagram illustrating an example of a configuration of a medical institution according to an exemplary embodiment. An institution 10 may include a hospital, a clinic, an emergency medical systems (EMS) agency, or other institution that provides medical services and whose providers are called upon to perform cardiac resuscitation of patients. The institution 10 includes one or more workstations 20 that each run a web browser 22. The workstations 20 are communicatively coupled to a database server 50 through a network 30 such as the Internet. The database server 50 also runs a web server 40. The network 30 is not particularly limited, and may be the Internet, or a local area network (LAN) or wide area network (WAN) depending on the needs of the institution. For example, a small clinic might have workstations implemented on a LAN rather than being connected internally to the Internet. The database server 50 is communicatively coupled to and accesses a database 60 such as a relational database. While only one institution 10 is shown in FIG. 1, the configuration is not limited to one institution, and a plurality of different institutions, each having a similar setup, and communicatively coupled together via the Internet 30 may be provided. For example, a clinic may be communicatively coupled to a hospital through the Internet 30.

Each institution has different capabilities in terms of, for example, personnel, medical equipment and capabilities available to treat patients, and the level of scientific evidence and materials available. Thus, for example, a hospital would include physicians and nurses along with a broad range of medical machines, equipment and capabilities, while a clinic might only be staffed with nurses and have more limited access to medical equipment. On the other hand, an EMS agency may have access to cutting edge life-saving technologies and equipment in specific medical areas, but be staffed with volunteer responders. As such the individual institutions and providers present different training challenges.

Figure 2:
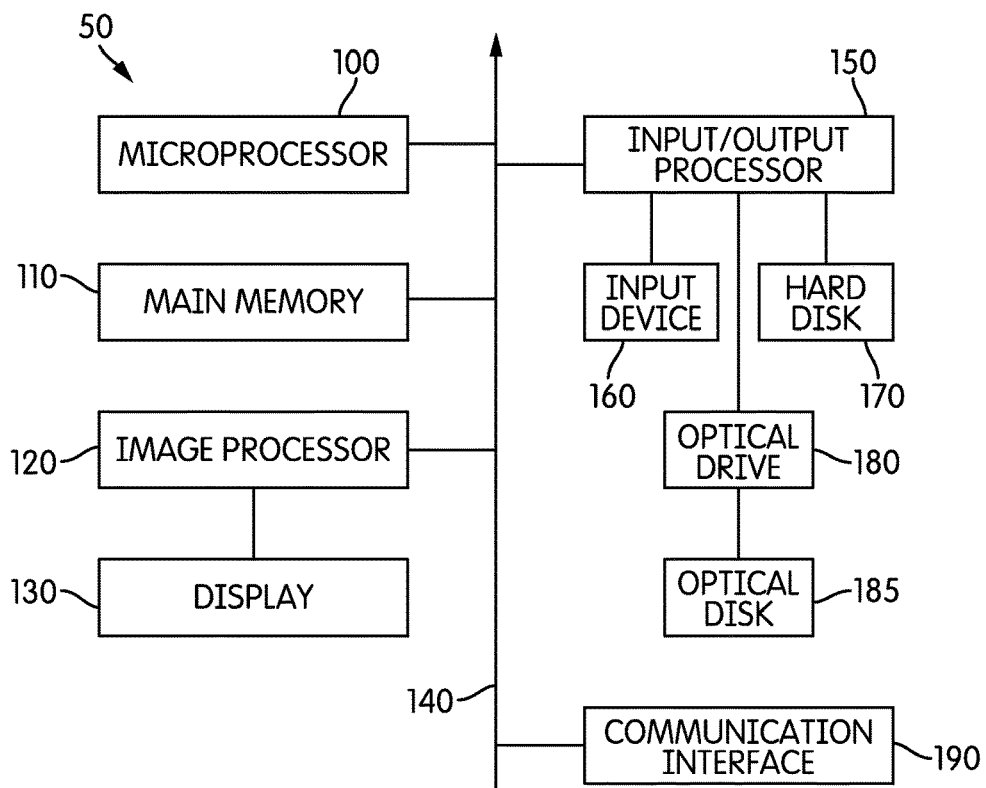
FIG. 2 is a structural view of a network system configuration of the database server of FIG. 1, according to an exemplary embodiment.

FIG. 2 illustrates an example configuration of the database server of FIG. 1. Turning to FIG. 2, the database server 50 includes microprocessor 100 (also known as a central processing unit (CPU)), an input device 160, a display 130, an optical drive 180, and a hard disk 170. The display 130 and the input device 160 are electrically connected to the database server 50. The optical drive 180 receives an optical disk 185, and is equipped in the database server 50. The input device 160 may include one or more of a mouse, a keyboard, a keypad, an optical pointer, a touchscreen, a touch pad, or the like.

The database server 50 further includes a bus 140, the microprocessor 100, a main memory 110, an image processor 120, an input/output processor 150, an optical drive 180, the input device 160, a hard disk 170, and a communication interface 190.

The bus 140 is provided for exchange of addresses and data among the elements of the database server 50. The microprocessor 100, the main memory 110, the image processor 120, and the input/output processor 150 are connected by the bus 140 to allow mutual data communication.

The microprocessor 100 controls the elements of the database server based on an operating system stored in a ROM (not shown) and a program and data which are read from an optical disk inserted into the optical drive 180 or from the hard disk 170. The main memory 110 includes, for example, a RAM. In the main memory 110, the program and data which are read from the optical disk or the hard disk 170 are written as necessary. The main memory 110 is also used as a work memory of the microprocessor 100.

The image processor 120 comprises a VRAM. The image processor 120 draws a graphical user interface (GUI) in the VRAM based on image data which is sent from the microprocessor 100. The GUI may be, for example, a web page. The image processor 120 converts the GUI into a video signal and outputs the video signal to the display 130 at a predetermined timing. The image processor 120 may also send the image data of the GUI to the web server 40 for serving up to web browsers 22 of various ones of the workstations 20. See FIG. 1.

The input/output processor 150 is an interface for the microprocessor 100 to access the optical drive 180, the input device 160, and the hard disk 170. The optical drive 180, the input device 160, and the hard disk 170 are electrically connected to the input/output processor 150.

In response to the image processor 120 displaying the GUI on the display 130, the input device 160 is manipulated in order to provide input and/or commands to the database server 50 through the GUI. The input and/or commands entered using the GUI may be stored in the hard disk 170. The commands may be processed by the microprocessor 100.

The optical drive 180 reads the program and data recorded on the optical disk 185 according to an instruction from the microprocessor 100. In this configuration, the optical disk is used for supplying the program and data to the database server 50, but it is also possible to supply the program and data to the database server 50 using any of other information storage media, such as a ROM card. In addition, the program and data may be supplied to the database server 50 from a remote location through a communication network such as, for example, the Internet 30.

The hard disk 170 is a typical hard disk device (auxiliary storage device). The hard disk 170 stores programs and data. For example, sensor data, data entered using the GUI, or the like may be stored in the hard disk 170. The communication interface 190 is an interface for connecting the database server 50 to a communication network such as the Internet in a wired or wireless fashion. While the communication interface 190 is shown in FIG. 2 as connected to the bus 140, it is also possible to connect the communication interface 190 to the input/output processor 150. Additionally, since the database server 160 communications with a plurality of workstations 20, more than one communication interface 190 may be provided.

The hardware configuration of the workstation 20 is similar to that of the database server 50 and thus a configuration of the workstation 20 will not be separately described. However, in addition to the above described components, the workstation 20 may include a sound processor and a speaker connected to the input/output processor 150 for providing sound output to the user of the workstation 20. Moreover, the workstation 20 may be provided with one or more sensors for taking measurement data on a patient. Examples of data that may be taken by the sensors are not particularly limited, and may include, for example, heart rate data, blood pressure data, temperature data, and the like. The input/output processor 150 scans states of the sensors every certain period. The input/output processor 150 sends an operation signal indicating the scan result through the bus 140 to the microprocessor 100. It is also possible to provide the database server 50 with sensors to collect any data that may be useful in diagnosing and treating a patient. However, in a case where the server is not provided in a patient area, it may not be advantageous to provide the server 160 with sensors for sensing patient data.

In the database server 50 having the above-described structure, a program which is read from the optical disk or the hard disk 170 is executed by the microprocessor 100.

The above-described database server 50 alone or in conjunction with the one or more workstations 20 carry out the automated advanced resuscitation training generation system. The automated advanced resuscitation training generation system is realized by executing one or more programs stored on an optical disk or a hard disk of the database server 50.

Overview of Training Generation System

Figure 3:
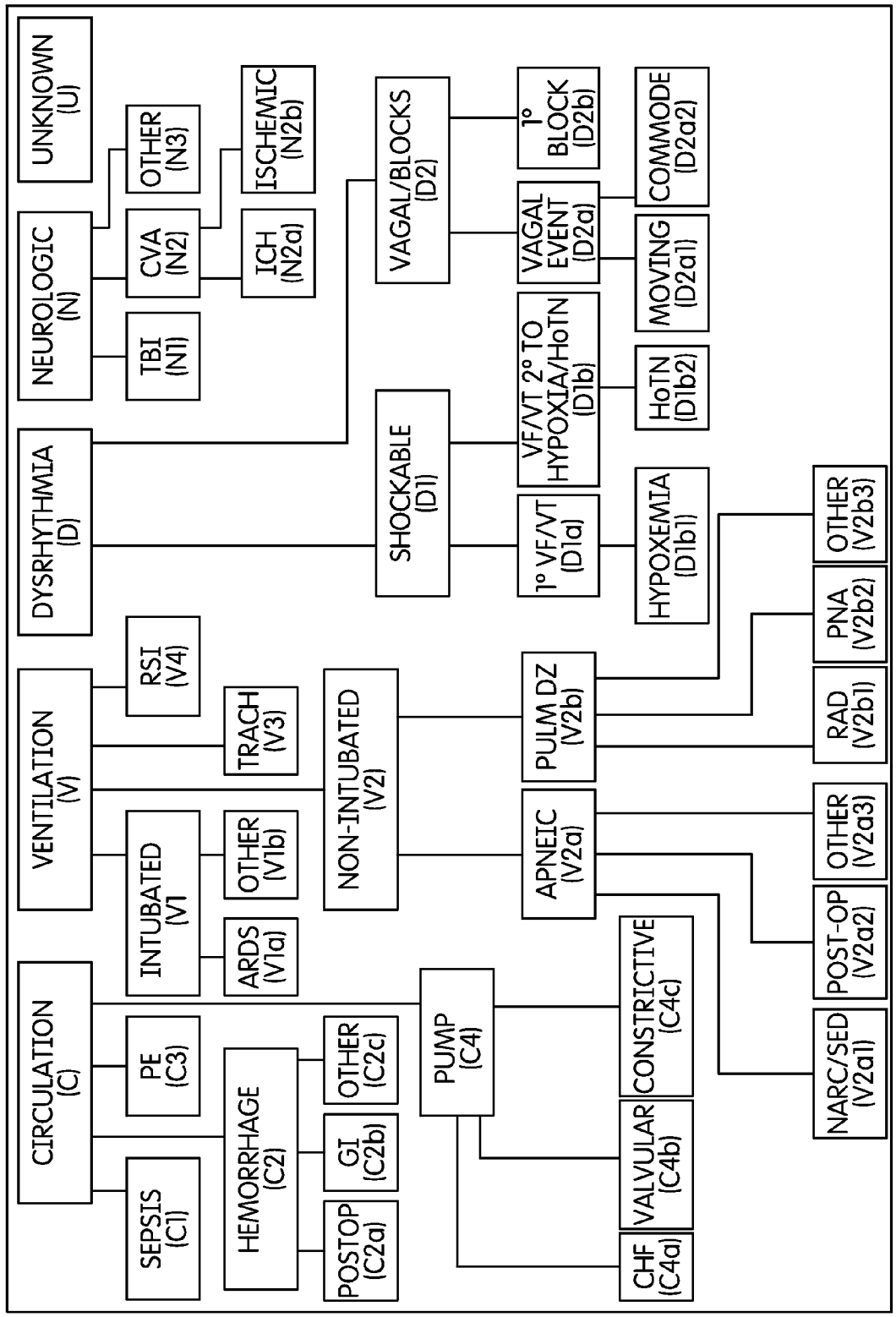
FIG. 3 shows an exemplary embodiment of the resuscitation matrix.
Figure 4:
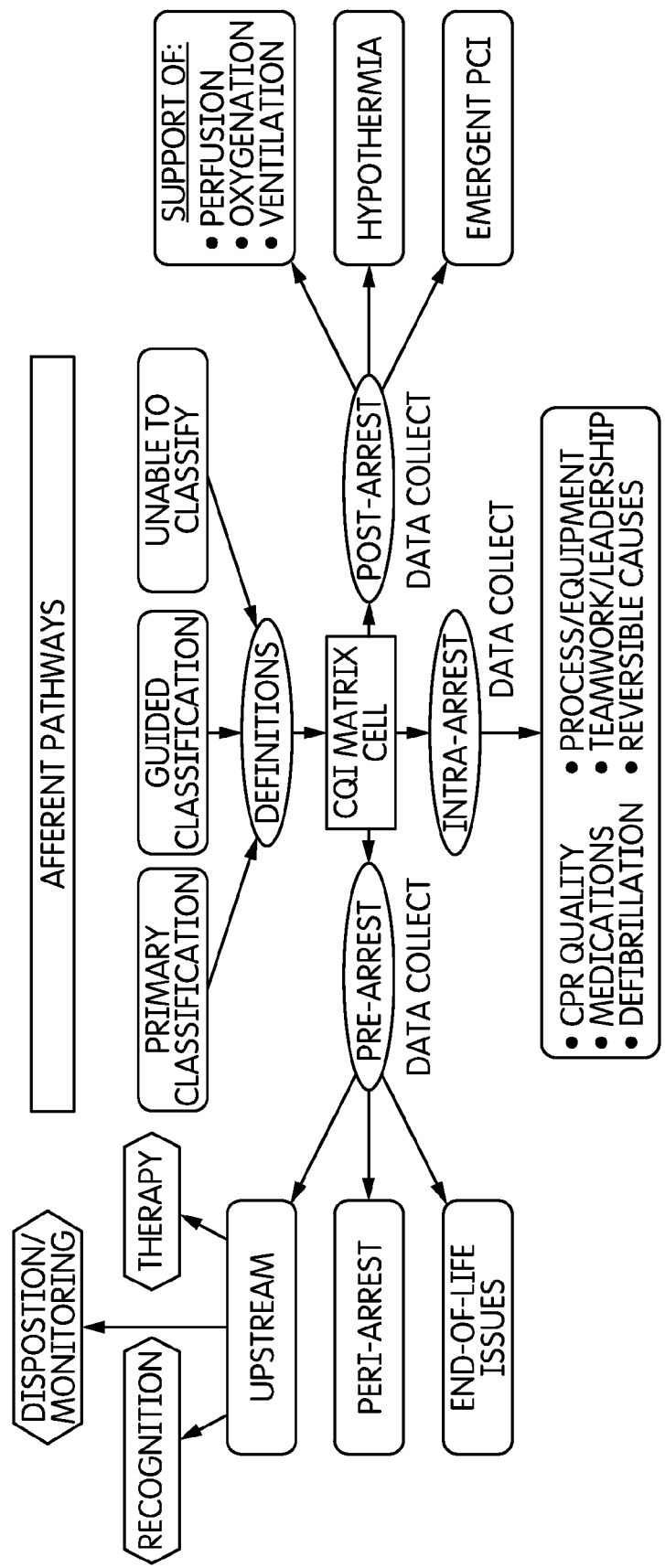
FIG. 4 shows an example of types of afferent pathways according to an exemplary embodiment.
Figure 5:
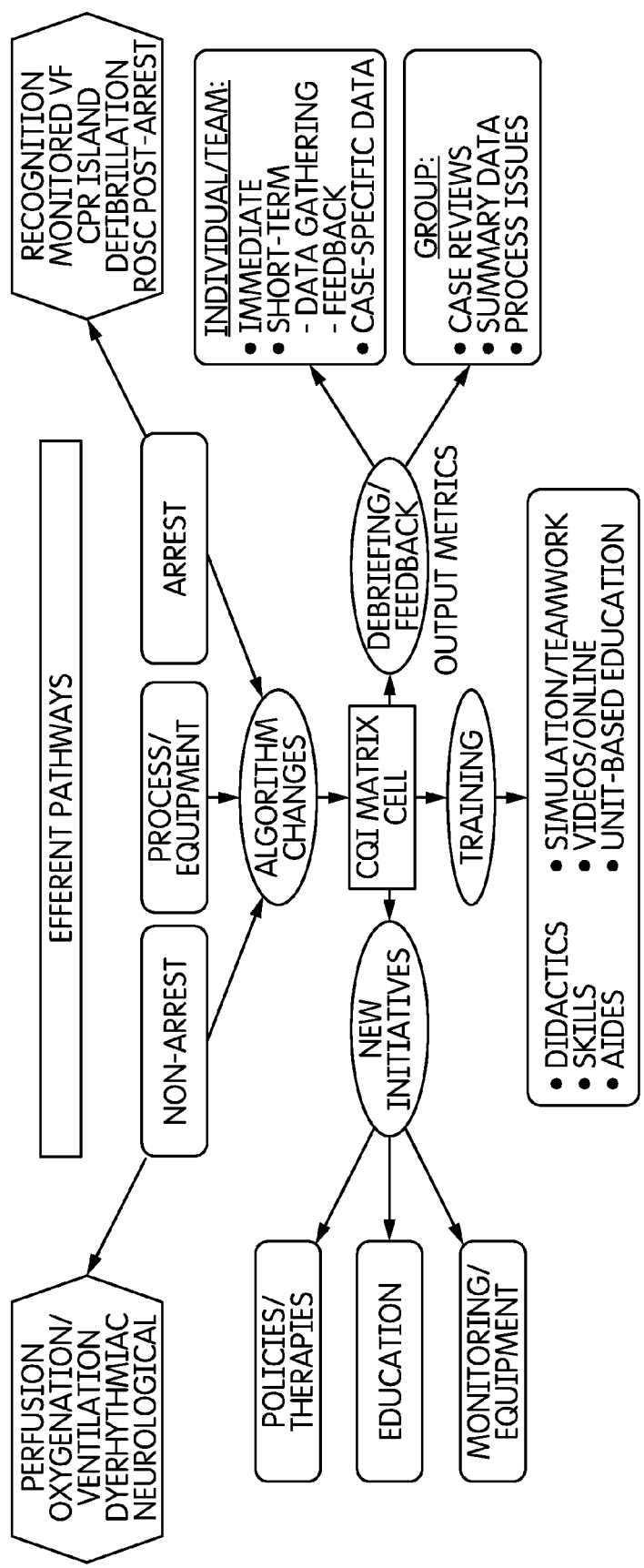
FIG. 5 shows an example of types of efferent pathways according to an exemplary embodiment.

The automated advanced resuscitation training generation system according to exemplary embodiments links continuous quality improvement (CQI) data with training, treatment algorithms, and special projects and initiatives. The CQI process uses a resuscitation matrix, which represents a sophisticated taxonomy to describe the various etiologies of cardiopulmonary arrest. An example of the resuscitation matrix is shown in FIG. 3. The matrix is hierarchical and allows for categorization of resuscitation events into discreet boxes. Each category implies a specific set of CQI "afferent" and "efferent" pathways as shown in FIGS. 4-5, respectively. Afferent pathways involve additional data collection, unique to the particular category, designed to investigate events leading up to a cardiac arrest. Efferents ultimately provide a series of graphical displays and dashboards that assess overall performance, monitor specific key metrics, and identify opportunities. Efferent pathways involve various reactions to CQI data, which may occur in response to a specific event (e.g., debriefing, dashboards to give feedback on specific metrics) or to summary data over the whole institution (e.g., changes in training, new projects or initiatives, modifications to treatment algorithms).

Figure 6:
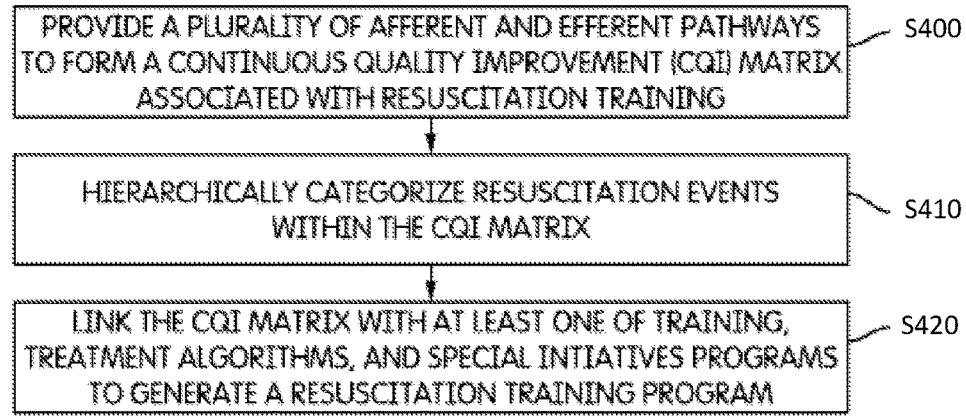
FIG. 6 shows an example of a process of generating a resuscitation training program according to an exemplary embodiment.

FIG. 6 illustrates the generation of a resuscitation training program. At operation S400, a plurality of afferent and efferent pathways are provided to form a continuous quality improvement (CQI) matrix associated with resuscitation training. At operation S410, resuscitation events are hierarchically categorized within the CQI matrix. At operation S420, the CQI matrix is linked with at least one of training, treatment algorithms, and special initiatives programs to generate the resuscitation training program.

The training is multi-modal, with a variety of platforms and an emphasis on shorter, more frequent exposures. Three basic training components are defined: didactics; psychomotor skills; and integrated simulation. Didactics may involve interactive lectures, videos, or web-based content, and are targeted to specific provider groups. Psychomotor skills sessions focus on CQI metrics and equipment used in clinical practice and may be performed on clinical units. Integrated simulation is multi-disciplinary, again utilizing actual equipment and focusing on specific scenarios identified using CQI data. For the hospital, training is organized under provider- and unit-specific tracks, such as for critical care physicians/nurses or for non-critical care providers. Respiratory Therapists participate in respiratory training, while pharmacists receive advanced resuscitative training emphasizing medication management. Content is modified to address resuscitation roles (Code MD or RN, rapid response team members) and patient units (surgical, medical, cardiac, obstetric, peri-operative). For the pre-hospital environment, the goal is to integrate teams. Modular training allows universal exposure to basic concepts, with additional didactics and skills training for advanced practitioners.

The training elements for didactics, psychomotor skills, procedures, and simulation are assembled in a modular fashion based on institutional CQI data, individual deficiencies, and instructor/leadership preferences, and/or based on provider type and course objectives Skills sessions and simulation (both online and using human patient simulators) are integrated with didactics and focus on specific skills, and a unique set of resuscitation algorithms. Thus, specific features of the program are designed for each institution (hospital or EMS agency, etc.). The training program further includes implementation tools and strategies for scheduling courses and estimating resource allocation, and includes a unique dataset that provides the substrate for the resuscitation matrix, and an original set of metrics. The training program and the matrix also link to a set of inpatient initiatives and special projects, designed to target particular issues and opportunities.

Thus, the resuscitation training program uses performance improvement data to guide resuscitation training.

Figure 7:
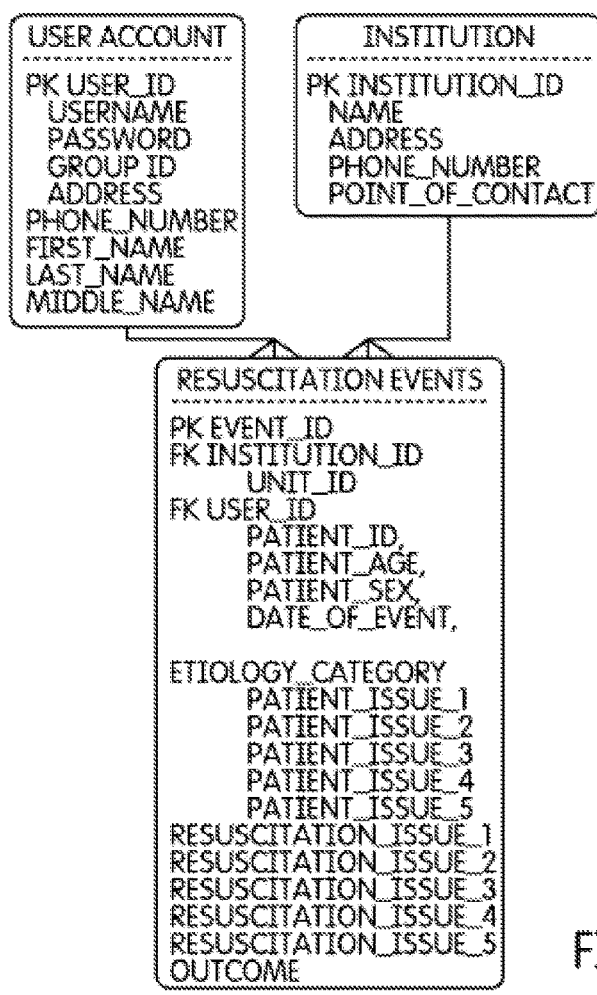
FIG. 7 shows an example of resuscitation event data according to an exemplary embodiment.

In more detail, in the automated advanced resuscitation training generation system, resuscitation event data is acquired by one or more of the workstations by displaying a GUI image on the display and receiving input using the input device. The resuscitation event data may be acquired from a provider who is giving care to a patient, or by one of the team members of the provider, and may be acquired during and/or after the resuscitation event. FIG. 7 shows an example of resuscitation event data that is acquired. The resuscitation event data is then stored in event database on the server for the institution. As part of the resuscitation event data, the event is classified according to a matrix. The matrix is separately maintained and represents a taxonomy to describe the various etiologies of cardiopulmonary arrest. The matrix is hierarchical and the resuscitation event is categorized into one or more discrete boxes within the matrix.

Figure 8:
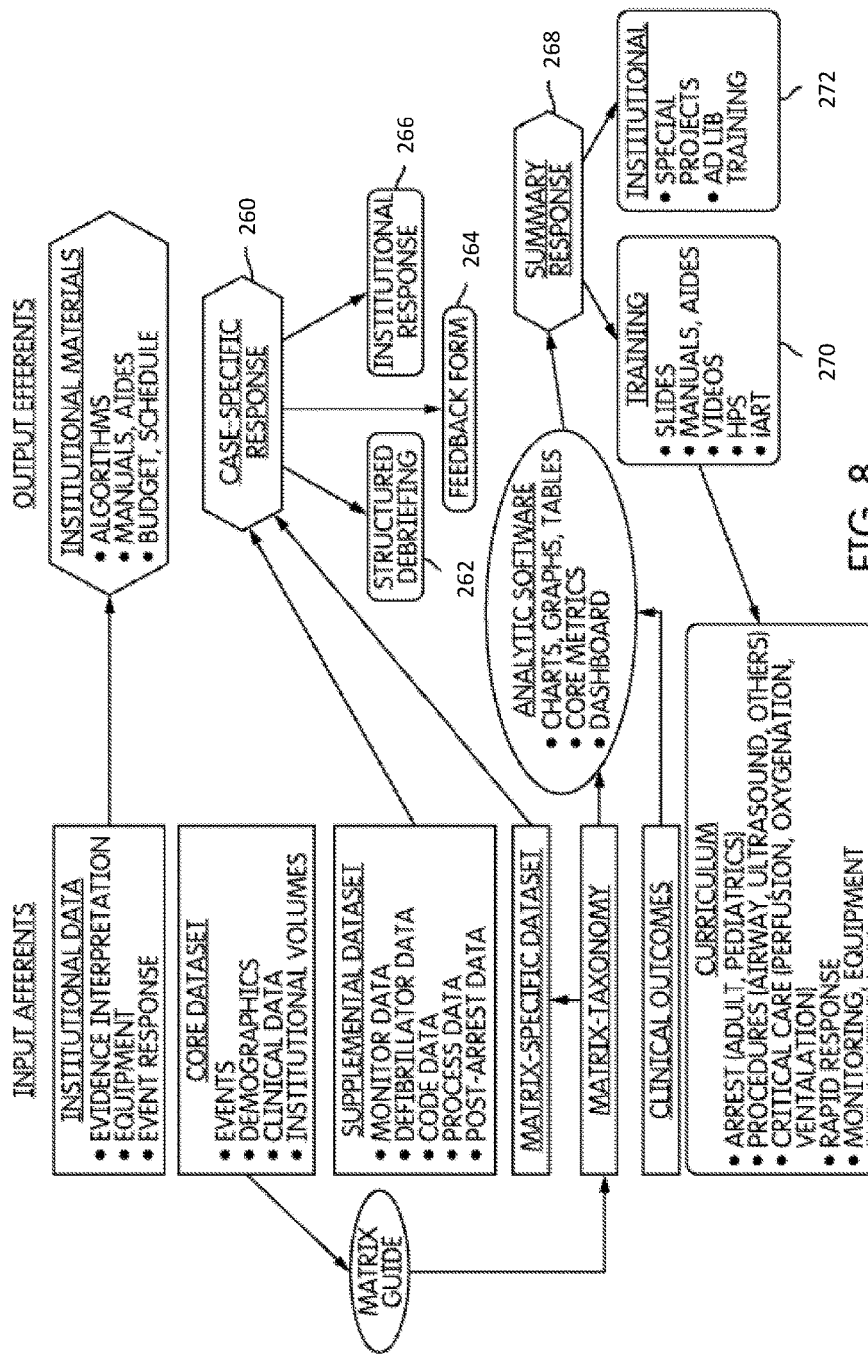
FIG. 8 shows an example of links between afferent pathways and efferent pathways, according to an exemplary embodiment.

Based on the categorization, i.e., the discrete boxes, of the individual resuscitation event, afferent data is generated and collected according to afferent pathways indicated by the categorization(s). That is, each category (i.e., discrete box or cell) is linked to a specific set of continuous quality improvement (CQI) afferent and efferent pathways. FIG. 8 shows an example of the link between the afferent pathways and the efferent pathways. The afferent pathways indicate additional data to be collected that is specific to the particular category or box. See FIG. 4. As shown in FIG. 4, the afferent data investigates additional events that lead up to the resuscitation event. The afferent data is added to the resuscitation event data and stored in the event database on the server.

Thereafter, based on the categorization, i.e., the discrete boxes, of the individual resuscitation event, efferent outputs are also generated according to the efferent pathways indicated by the categorization(s). See FIG. 5. As shown in FIG. 5, for example, a case specific response is generated for the individual resuscitation event based on the matrix categorization (i.e., the discrete box or cell) and the resuscitation event data. The efferent pathways provide links between the matrix categories and graphical displays and dashboards that assess overall performance, monitor specific key metrics, and identify training opportunities.

The resuscitation event data for a specific individual patient is also combined with resuscitation event data of other patients from the same institution in order to generate summary data according to the CQI afferent and efferent pathways. Thus, as shown in FIG. 8, the efferent pathways also involve various reactions to CQI data on a summary level, providing for, for example, changes in training, new project initiatives, modifications to treatment algorithms, etc.

Based on the efferent pathways and the matrix categories, a training program is generated using a separately maintained database of training components. The training components are modular and include didactics, psychomotor skills, and integrated simulation according to the different efferent pathways. The training program for didactics, psychomotor skills, procedures, and simulation are assembled in a modular fashion based on the institutional summary data, the individual resuscitation event data, and pre-stored training information in order to provide relevant training both to individual primary care providers such as doctors, nurses, clinicians, and EMTs, but also institutional training to specific groups such as respiratory therapists, pharmacists, and different teams such as surgical medical, cardiac, obstetric teams.

Below a technology for automatically generating an advanced resuscitation training program will be described.

Figure 9:
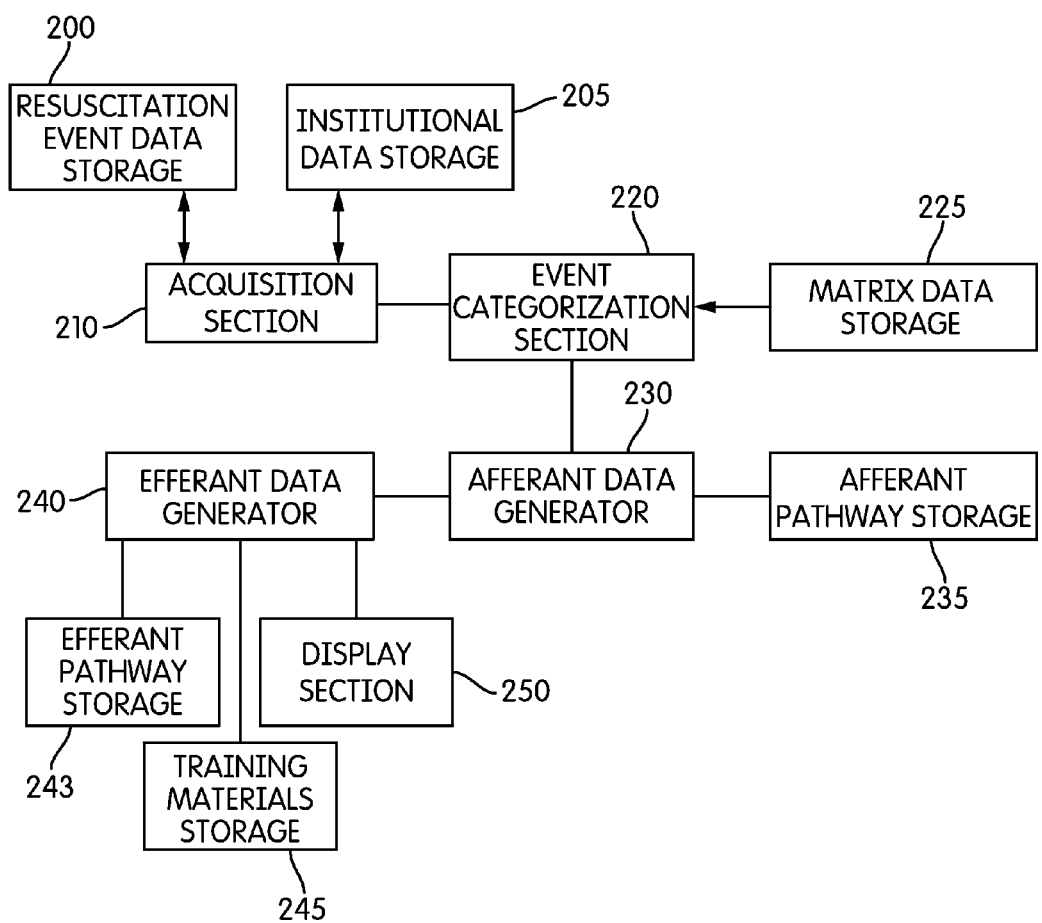
FIG. 9 is a functional block diagram showing functions according to exemplary embodiments.

FIG. 9 is a functional block diagram showing functions according to exemplary embodiments. As shown in FIG. 9, the automatic advanced resuscitation training generation system includes a resuscitation event data storage 200, an institutional data storage 205, an acquisition section 210, a matrix data storage 225, an event categorization section 220, an afferent pathways storage 235, an afferent data generator 230, an efferent pathways storage 243, a training materials storage 245, an efferent data generator 240, and a display section 250.

The resuscitation event data storage 200 is realized, mainly, using, e.g., the main memory 110 and/or the hard disk 170 of the database server 50. Alternatively, the resuscitation event data storage 200 may be realized using the main memory 110 and/or the hard disk 170 of one or more workstations 20 and/or the database server 50 in a distributed environment.

The resuscitation event data storage 200 stores various data concerning a resuscitation event of individual patients. For example, the resuscitation event data storage 200 stores data including, for example, an event identifier (ID), an institution ID, an in-hospital or out-of-hospital unit ID or flag, a data entry actor ID, a primary care physician ID, a patient ID, a patient age, a patient sex, a date of the resuscitation event, an admitting service, a hospital unit, one or more patient issues, one or more etiology categories of the resuscitation event, one or more resuscitation issues, an outcome of the resuscitation procedure, and an optional field for context recording, etc. The amount and type of data is not particularly limited, but generally the resuscitation event data is data that would typically be generated and recorded during and/or after a resuscitation event. While many of the fields are indicated as IDs, it will be understood that the IDs may alternatively be flags, string text, or other types of data that indicate the information of the field.

The institution data storage 205 is realized, mainly, using, e.g., the main memory 110 and/or the hard disk 170 of the database server 50. Alternatively, the institution data storage 205 may be realized using the main memory 110 and/or the hard disk 170 of one or more workstations 20 and/or the database server 50 in a distributed environment.

The institution data storage 205 stores various data concerning an institution which has handled the resuscitation event. For example, the institution data storage 205 stores data including, for example, an institution ID, an institution name, an institution address, an institution phone number, and an institution point of contact person, etc. As with the resuscitation event data, the amount and type of data is not particularly limited, but generally the institution data is data about the institution that is not particular to an individual patient. It will be understood that the data types may be IDs, flags, string text, or the like as appropriate for the type of information. While the institution data storage 205 is shown as a separate physical storage in FIG. 9, the institution data storage may be provided as a logical portion of the resuscitation data storage 200, or the institution data of the institution data storage 205 may be integrated together with the resuscitation data in the resuscitation data storage 200.

The acquisition section 210 is realized mainly, e.g., using the microprocessor 100 and the main memory 110 of the database server 50. Alternatively, the acquisition section 210 may be realized using the main memory 110 and/or the hard disk 170 of one or more workstations 20 and/or the database server 50 in a distributed environment.

The acquisition section 210 generates and sends image data to generate a GUI at the one or more of the workstations for generating, populating, modifying and deleting resuscitation event data and/or institutional data, and acquires the resuscitation event data and/or the institutional data from the workstations. That is, the acquisition section 210 may send the image data through the web server 40 to the web browser 22 of one or more workstations. The GUI may include pick lists, drop down lists, text entry boxes and/or other appropriate devices for data entry. The acquisition section 210 also performs range checking and error correction on the acquired data to ensure proper entry of the resuscitation event data and/or the institutional data. The resuscitation event data and/or institutional data may be entered by the individual provider who performed the resuscitation or by the team of the individual provider. The institutional data may be entered by an appropriate person associated with the institution. Alternatively, the individual provider or the team of the individual provider may enter both the resuscitation event data and the institutional data. The resuscitation event data and/or the institutional data may be, in full or in part, automatically populated from other sources within the institution. For example, some portion of the resuscitation event data may be entered by sensing a bar code or QR code located with the patient or may be entered by downloading from one or more pieces of medical equipment.

The matrix data storage 225 is realized, mainly, using, e.g., the main memory 110 and/or the hard disk 170 of the database server 50. Alternatively, the matrix data storage 225 may be realized using the main memory 110 and/or the hard disk 170 of one or more of the workstations 20 and/or the database server 50 in a distributed environment.

The matrix data storage 225 stores the matrix data of etiologies of resuscitation. An example of the matrix is provided in FIG. 3. As discussed above, the matrix represents a taxonomy to describe the various etiologies of cardiopulmonary arrest. The matrix is hierarchical and categorizes the resuscitation events into discrete boxes or cells. As shown in FIG. 3, the matrix includes a first tier of the hierarchy that includes circulation, ventilation, dysrhythmia, neurologic, and unknown causes. Under circulation, a second tier of the hierarchy includes sepsis, hemorrhage, PE, and pump, and so on. The matrix data storage 225 allows the matrix data to be independently updated as new categories are added to the taxonomy. This ability for independent updating of the matrix provides a part of the flexibility of the inventive concept disclosed herein.

The event categorization section 220 is realized mainly, e.g., using the microprocessor 100 and the main memory 110 of the database server 50. Alternatively, the acquisition section 210 may be realized using the main memory 110 and/or the hard disk 170 of one or more workstations 20 and/or the database server 50 in a distributed environment.

Figure 10A:
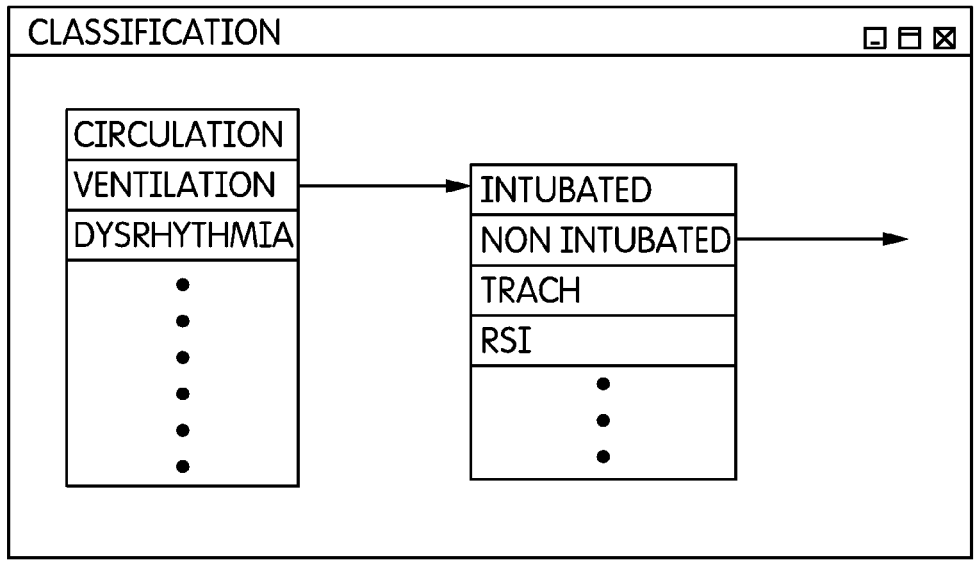
FIGS. 10A and 10B are examples of graphical user interfaces (GUIs) according to exemplary embodiments.
Figure 10B:
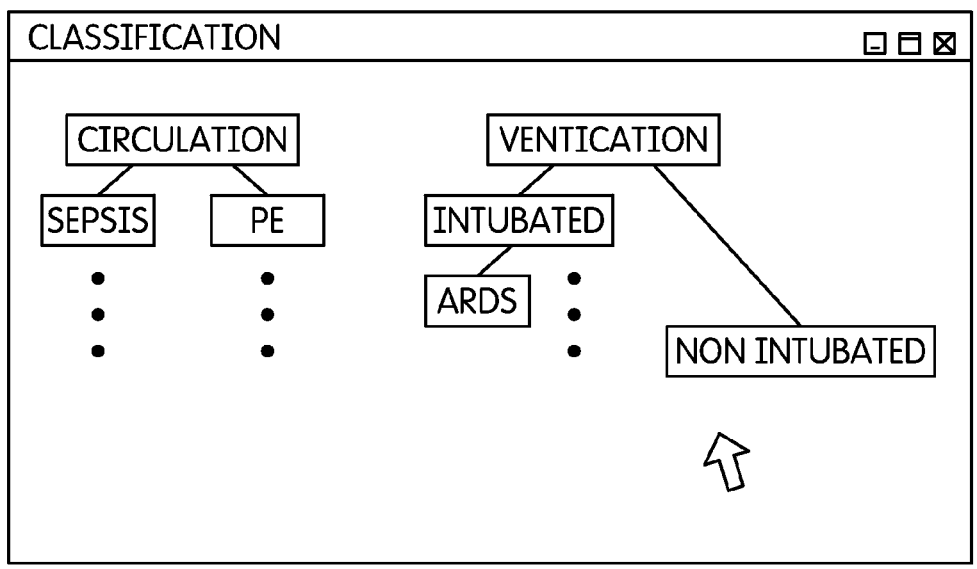

The event categorization section 220 reads the matrix from the matrix data storage 225 and uses the read matrix information to generate and send image data to one or more workstations to display a GUI by which the categorization is performed. That is, the acquisition section 210 may send the image data through the web server 40 to the web browser 22 of one or more workstations. For example, the GUI may include a plurality of selection windows, as shown in the example in FIG. 10A. Alternatively, the GUI may include a clickable image depicting the hierarchy on which a user may click one or more boxes to perform the categorization, as shown in FIG. 10B. Alternatively, the GUI may display pick lists, drop down lists, scrolling lists, or text entry boxes appropriate for entering the hierarchical selection information. The event categorization section 220 also performs error checking and correction to ensure proper entry of the categories according to the matrix. The event categorization section 220 may receive input of a primary classification. Alternatively, the event categorization section 220 may provide a guided classification in which a classification is suggested based on one or more of the resuscitation event data points. The event categorization section 220 receives a selection of one or more categories associated with the individual resuscitation event by either primary classification or guided classification. The one or more categories are added to the resuscitation event data and stored in the resuscitation event data storage 200.

The afferent pathway storage 235 is realized, mainly, using, e.g., the main memory 110 and/or the hard disk 170 of the database server 50. Alternatively, the afferent pathway storage 235 may be realized using the main memory 110 and/or the hard disk 170 of one or more workstations 20 and/or the database server 50 in a distributed environment.

The afferent pathway storage 235 stores afferent pathways in association and corresponding to each of the matrix categories, i.e., afferent pathways for each discrete box or cell, and also general afferents that are unrelated to the matrix categories. For example, each discrete category may be provided with an ID, and the afferent pathways linked to the discrete category using the ID. A schematic illustration of an example of afferent pathways is shown in FIG. 4. As discussed above, the general afferents include sources of information such as, for example, information stored in databases throughout the institution, monitor and/or sensor data, scientific literature, etc., that help document performance and inform decision making. The afferent pathways indicate additional category-specific afferents. These category-specific afferents provide additional data points for collection that are unique to the particular category. The afferent pathways are designed to investigate events leading up to the resuscitation event. FIGS. 11A-11H illustrate examples of the types of afferent data that may be collected for a given category. It will be understood that the afferent data in FIGS. 11A-11H are merely examples of the types of afferent data that might be of interest. The particular afferent pathways may be the same as or different for each discrete category. As with the matrix data, the afferent pathway storage 235 allows the afferent pathways to be independently updated as new afferent pathways are found to be relevant or not relevant to a particular category.

The afferent data generator 230 is realized mainly, e.g., using the microprocessor 100 and the main memory 110 of the database server 50. Alternatively, the afferent data generator 230 may be realized using the main memory 110 and/or the hard disk 170 of one or more workstations 20 and/or the database server 50 in a distributed environment.

The afferent data generator 230 reads the afferent pathways from the afferent pathway storage 235 that are associated with the one or more categories into which the resuscitation event has been categorized by the event categorization section 220, and the general afferents. The afferent data generator 230 than generates afferent data based on the afferent pathways and the general afferents. The afferent data may be automatically populated from other sources within the institution. For example, the afferent data generator 230 may pull afferent data from a workstation that has one or more sensors, or attached medical equipment, for recording CPR Process Metrics. See FIG. 11E. The afferent data generator 230 may also access one or more external databases that include afferent information, for example antecedent data or information about bystander CPR. See FIGS. 11C and 11D. In some instances, such databases may be external to the institution and thus may be accessed through the internet from another institution. See FIG. 1. Non-limiting examples might be data recorded by EMS responders and stored in a database at the EMS responder, or EEG data entered at a clinic which the patient has used in the past. See FIGS. 11D and 11F. Additionally, the afferent data generator 230 may generate data by sensing a bar code or QR code located with the equipment that has the data or with a database that stores the data, or may be generated by downloading the afferent data from one or more pieces of medical equipment.

Depending on the afferent data to be generated, the afferent data generator 230 may in addition to or alternatively generate and send image data to a workstation to display a GUI at the workstation, and may acquire additional afferent data from the workstation through the GUI. That is, the afferent data generator 230 may send the image data through the web server 40 to the web browser 22 of one or more workstations. The GUI may include pick lists, drop down lists, text entry boxes and/or other appropriate devices for afferent data entry. The afferent data generator 230 may also perform range checking and error correction on the afferent data acquired from the workstation to ensure proper entry of the resuscitation event data and/or the institutional data.

The efferent pathway storage 243 is realized, mainly, using, e.g., the main memory 110 and/or the hard disk 170 of the database server 50. Alternatively, the efferent pathway storage 243 may be realized using the main memory 110 and/or the hard disk 170 of one or more workstations 20 and/or the database server 50 in a distributed environment.

Figure 12E:
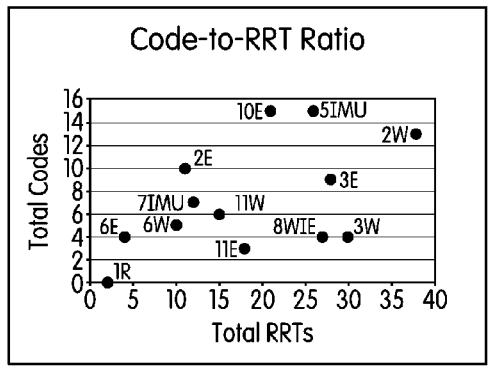
FIGS. 12A-12O illustrate examples of the types of efferent data that may be output for a given category.
Figure 12F:
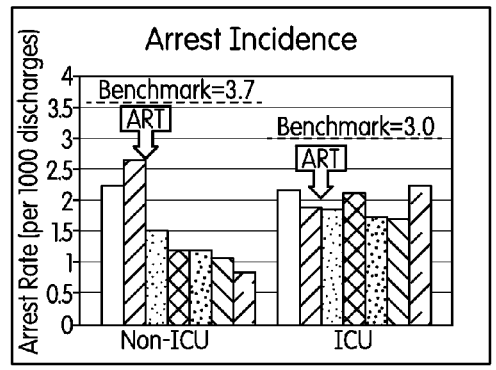
Figure 12G:
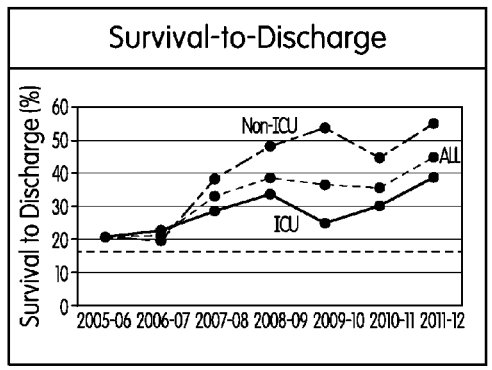
Figure 12H:
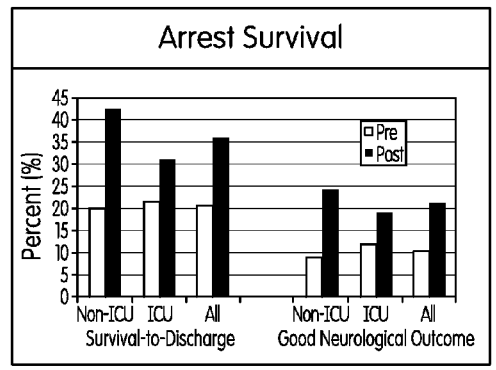
Figure 12I:
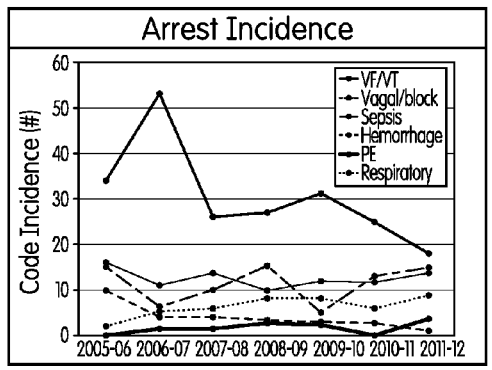
Figure 12J:
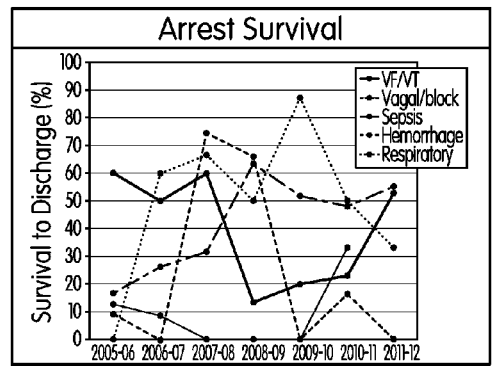
Figure 13B:
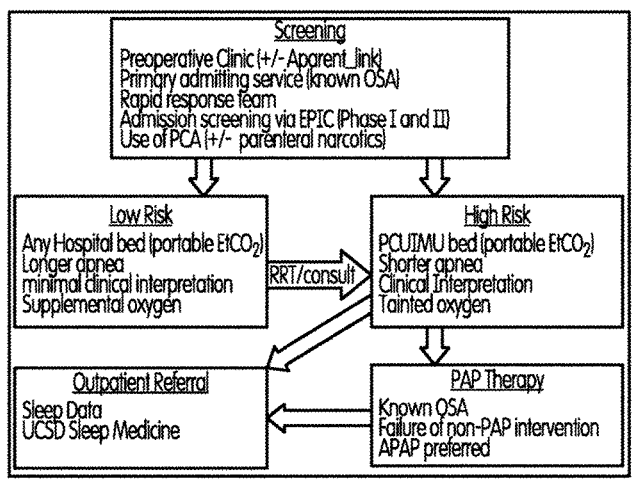
Figure 13C:
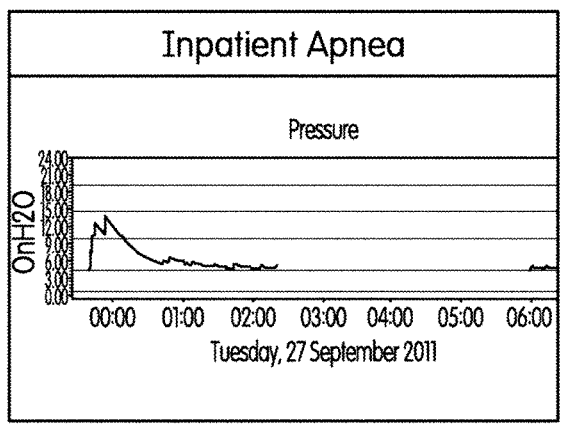
Figure 13D:
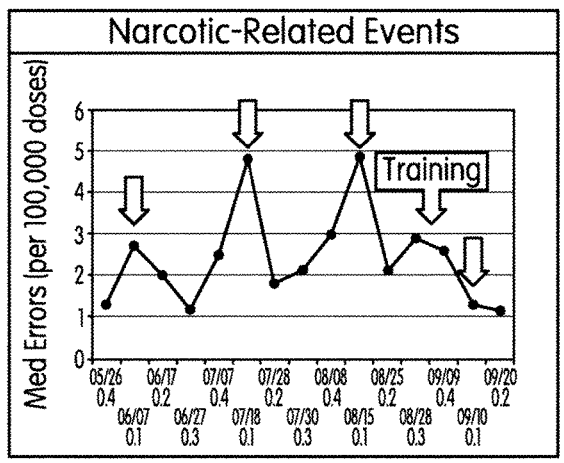

The efferent pathway storage 243 stores efferent pathways in association and corresponding to each of the matrix categories, i.e., efferent pathways for each discrete box or cell. For example, each discrete category may be provided with an ID, and the efferent pathways linked to the discrete category using the ID. A schematic illustration of an example of efferent pathways is shown in FIG. 5. As discussed above, the efferent pathways involve various reactions to CQI data, and may occur in response to a specific resuscitation event or in response to summary data of resuscitation events across an institution that indicate track/trend data. See FIGS. 5 and 8. The efferent pathways for a specific resuscitation event may include, for example, debriefing information, dashboards to give feedback, risk management response, or metrics. The efferent pathways in response to summary data may include, for example, changes in training; new projects, procedures, and/or protocols; the launch of new or targeted initiatives; the purchase and/or implementation of new equipment and technology; and/or modifications to treatment algorithms. FIGS. 12A-12O illustrate examples of the types of efferent data that may be output for a given category, and FIGS. 13A-13D illustrate examples of new project or initiatives. FIGS. 12A-12M illustrate efferent pathways in response to summary data, and include for example data on the arrest incidence and arrest survival rates for a hospital. FIGS. 12N-12O illustrate examples of efferent pathways for a specific resuscitation event, in this case involving follow-up debriefing on sleep apnea of the patient. It will be understood that the efferent pathways and data in FIGS. 12A-12O and 13A-13D are merely examples of the types of afferent data that might be of interest. The particular efferent pathways may be the same as or different for each discrete category. As with the matrix data, the efferent pathway storage 243 allows the efferent pathways to be independently updated as new efferent pathways are found to be relevant or not relevant to a particular category.

The training materials storage 245 is realized, mainly, using, e.g., the main memory 110 and/or the hard disk 170 of the database server 50. Alternatively, the training materials storage 245 may be realized using the main memory 110 and/or the hard disk 170 of one or more workstations 20 and/or the database server 50 in a distributed environment.

The training materials storage 245 stores a variety of multi-modal training materials. The training materials are multi-modal, with a variety of platforms. Three basic training components include didactics, psychomotor skills, and integrated simulation. Didactics materials may involve interactive lectures, videos, or web-based content, and are targeted to specific provider groups. Psychomotor skills sessions focus on metrics and equipment used in clinical practice and may be performed on clinical units. Integrated simulation is multi-disciplinary, again utilizing actual equipment and focusing on specific scenarios identified using afferent and efferent pathways. The training materials storage 245 stores the training materials in association and corresponding to each of the matrix categories, i.e., training materials associated with each discrete box or cell. For example, each discrete category may be provided with an ID, and the training materials may be linked to the discrete category using the ID. Additionally, the training materials may be stored in association with a ranking or priority that is individually set for the training material. The training materials may also include online education materials that are provided using links to web pages located over the Internet outside of the Institution. See FIG. 1.

The efferent data generator 240 is realized mainly, e.g., using the microprocessor 100 and the main memory 110 of the database server 50. Alternatively, the efferent data generator 240 may be realized using the main memory 110 and/or the hard disk 170 of one or more workstations 20 and/or the database server 50 in a distributed environment.

The efferent data generator 240 reads the efferent pathways from the efferent pathway storage 243 and the training materials that are associated with the one or more categories into which the resuscitation event has been categorized by the event categorization section 220. The efferent data generator 240 then generates a training program using a modular approach based on the read efferent pathways, the read training materials and the resuscitation event data. For example, the efferent data generator 240 may organize training materials for the hospital under provider- and unit-specific tracks, i.e. for critical care physicians/nurses or for non-critical care providers. If the resuscitation event data and category indicates respiratory issues, the efferent data generator 240 would output training materials for Respiratory Therapists, whereas pharmacists would receive advanced training emphasizing medication management. Thus, the training materials are generated and modified to address resuscitation roles (Code MD or RN, rapid response team members) and patient units (surgical, medical, cardiac, obstetric, peri-operative). For the pre-hospital environment, the goal is to integrate teams, and thus the efferent data generator 240 would generate training materials geared to a specific team. Modular training allows universal exposure to basic concepts, with additional didactics and skills training for advanced practitioners.

The display section 250 is realized mainly, e.g., using the microprocessor 100, the image processor 120, the display 130 of a workstation 20 or the database server 50. The display section 250 displays the above-described GUIs and displays the training materials generated by the efferent data generator 240.

While the above functional blocks have been described as being realized by the workstation or by the server, the present inventive concept is not limited to this configuration. That is, the functions described may be distributed across multiple devices on the network in a distributed system. Additionally, although the storages described above are described as separate, the storages may be provided as partitions of a single storage located somewhere on the network. Alternatively, the storages may be integrated together.

Below, a process to be carried out by the network system according to an exemplary embodiment will be described with reference to FIG. 14. The microprocessor 100 of a workstation, and/or the microprocessor 100 of a server carry out the process.

Figure 14:
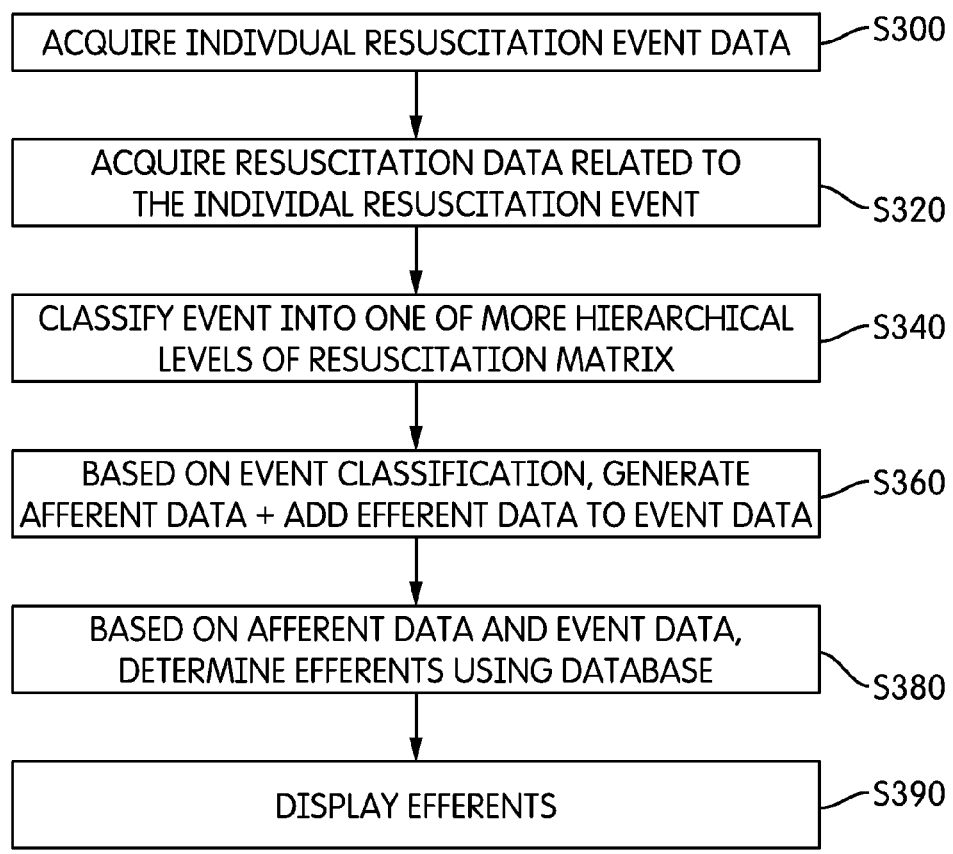
FIG. 14 is a process to be carried out by the network system according to an exemplary embodiment.

As shown in FIG. 14, the microprocessor 100 acquires individual resuscitation event data of a resuscitation event. (Operation S300). The event data may be acquired by displaying a GUI to a user and the user entering the resuscitation event data using the GUI and the input device 160. Alternatively, a portion or all of the resuscitation event data may be acquired from a database or other such storage on the network.

At Operation S320, the microprocessor 100 acquires institutional data related to the individual resuscitation event. The institutional data may be acquired by displaying a GUI for a user to enter the institution data, or alternatively, the institutional data may be acquired from a database or other storage located on the network. Alternatively, operation S320 may be performed along with operation S300.

At Operation S340, the microprocessor 100 categorizes the resuscitation event into one or more hierarchical categories of a resuscitation matrix. The resuscitation matrix is stored in the above-described matrix data storage.

At Operation S360, the microprocessor 100 generates afferent data based on the one or more categories, and adds the afferent data to the resuscitation event data.

At Operation S380, the microprocessor 100 determines efferents using efferent pathways based on the one or more categories, the generated afferent data and the resuscitation event data. At Operation S390, the microprocessor 100 displays the efferents.

Figure 15:
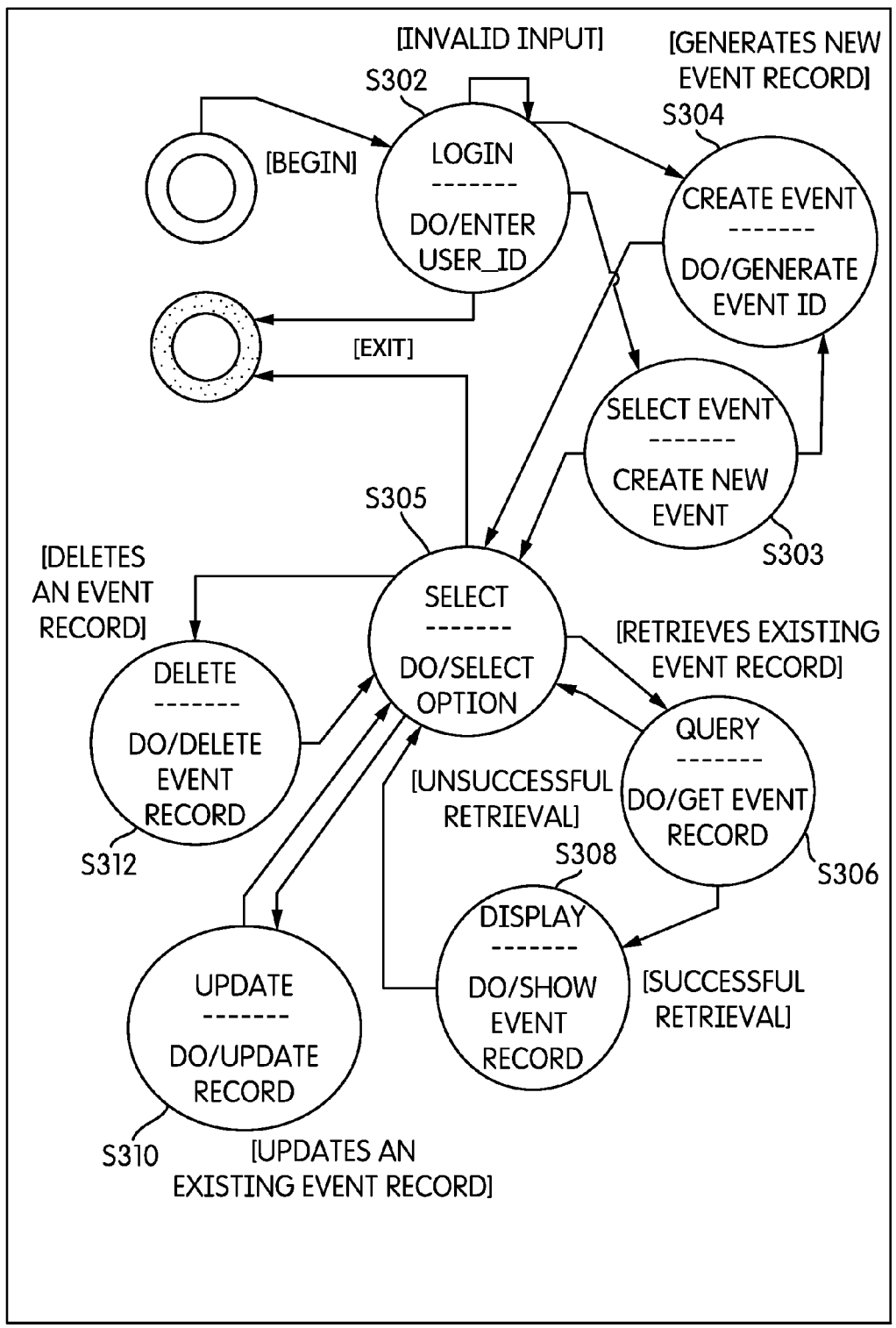
FIG. 15 is a flowchart showing the acquiring an individual resuscitation event data of FIG. 14 in more detail.

FIG. 15 is a flowchart showing the acquiring an individual resuscitation event data of FIG. 14 in more detail.

Initially, a GUI that provides a log in prompt is displayed on the display in S302. If the user, i.e. the Primary Provider, enters incorrect information, the process returns to S302. If the input is valid, the process proceeds to S303 where a GUI that provides a selection display in order to determine whether to create a new event or to select an existing event. When it is determined that a new event is to be created, the process proceeds to S304 where the event is assigned an event ID. When it is determined that an existing event is to be selected, the process proceeds to S305 where a GUI is displayed provides a selection display in order to determine whether to query or browse the event, update the event, view the event or delete the event. When it is determined to query or browse an event, the process proceeds to S306 where a GUI is displayed for entering query parameters. When it is determined to update an event, the process proceeds to S310 where a GUI is displayed for updating the data of the event. When it is determined to view an event, the process proceeds to S308 where a GUI is displayed showing the event data. When it is determined to delete an event, the process proceeds to S312 where a GUI is displayed requesting an event ID to delete. Once the event ID is entered, the event is deleted. After each of the operations S306, S308, S310, and S312, the process returns to operation S305.

Figure 16:
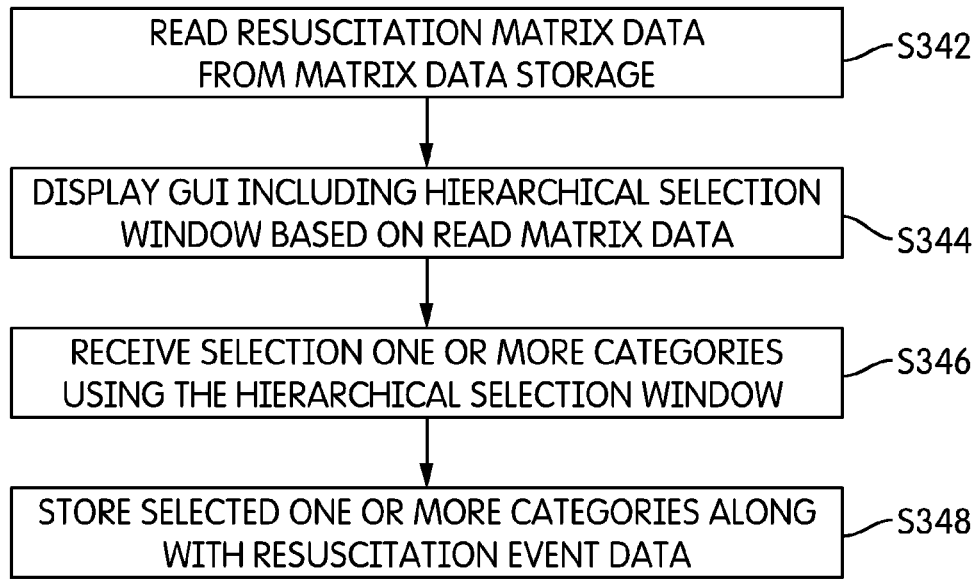
FIG. 16 is a flowchart showing the classification of the event of FIG. 14 in more detail.

FIG. 16 is a flowchart showing the classification of the event of FIG. 14 in more detail. Referring to FIG. 16, at operation S342, resuscitation matrix data is read from the matrix data storage. At operation S344, the microprocessor displays a GUI that includes a hierarchical selection window based on the read matrix data. Thereafter, a selection of one or more categories for the resuscitation event is received using the hierarchical selection window at S346. Finally, the selected one or more categories is stored with the resuscitation event data at S348.

Figure 17:
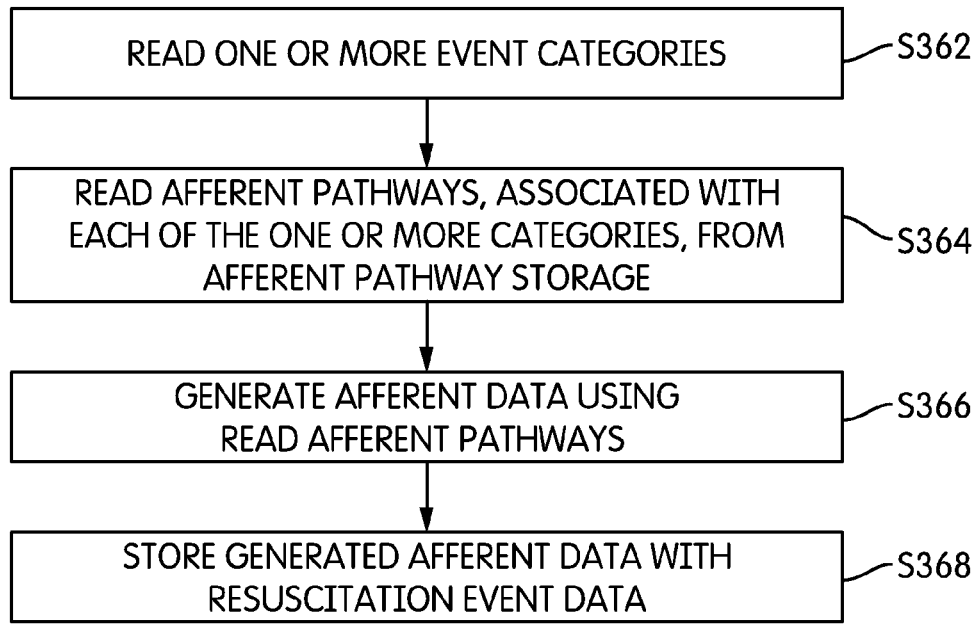
FIG. 17 is a flowchart showing the generation of afferent data of FIG. 14 in more detail.

FIG. 17 is a flowchart showing the generation of afferent data of FIG. 14 in more detail. Referring to FIG. 17, at operation S362, the one or more event categories are read. Then, afferent pathways corresponding to each of the one or more event categories are read from the afferent pathway storage at operation S364. At operation S366, afferent data is generated using the read afferent pathways as a guide. Finally, the generated afferent data is stored with the resuscitation event data in operation S368.

Figure 18:
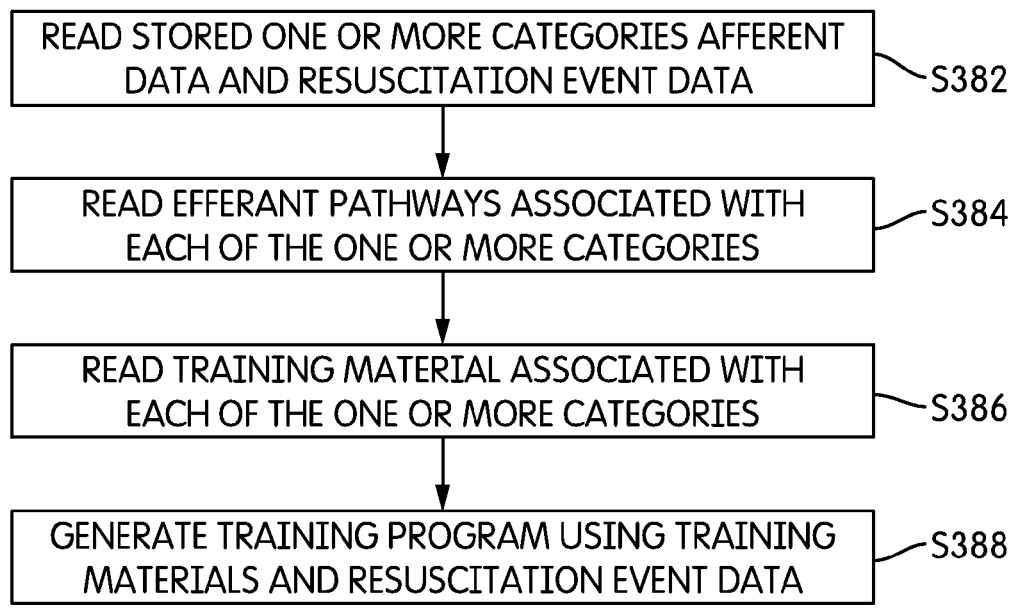
FIG. 18 is a flowchart showing the determination of efferents of FIG. 14 in more detail.

FIG. 18 is a flowchart showing the determination of efferents of FIG. 14 in more detail. Referring to FIG. 18, at operation S382, the stored one or more categories, afferent data, and resuscitation event data are read. The efferent pathways associated with each of the one or more categories are read from the efferent pathways storage in operation S384. The training materials associated with each of the one or more categories are read in operation S386. Finally, a training program is generated using the training materials, the afferent data, and the resuscitation event data in operation S388. Additional efferents may also be output.

Various exemplary embodiments described above are directed to a simplified institutional approach to resuscitation. Consideration is given to specific equipment and capabilities of a response team, integration of a broad spectrum of resuscitation concepts, use of data to modify treatment algorithms and training and guide new initiatives; and a flexible and adaptive training program that is responsive to the needs of the trainees. Unlike conventional, existing models of life support training, the present inventive concept recognizes the complexity of deterioration and incorporates cardiopulmonary arrest prevention, employing an original "Integrated Critical Care Model" to relate multiple components of resuscitation physiology, and defines a new paradigm for inpatient and pre-hospital medicine.

It will be understood that the present inventive concept can take the form of an entirely hardware embodiment, an entirely software embodiment or an embodiment containing both hardware and software elements. The present inventive concept may be implemented in software, which includes but is not limited to firmware, resident software, microcode, etc.

Furthermore, the present inventive concept can take the form of a computer program product accessible from a computer-usable or computer-readable medium providing program code for use by or in connection with a computer or any instruction execution system. A computer-usable or computer readable medium can be any tangible apparatus that can contain, store, communicate, propagate, or transport the program for use by or in connection with the instruction execution system, apparatus, or device. Examples of a computer-readable medium include a semiconductor or solid state memory, magnetic tape, a removable computer diskette, a random access memory (RAM), a read-only memory (ROM), a rigid magnetic disk and an optical disk. Examples of optical disks include compact disk-read only memory (CD-ROM), compact disk-read/write (CD-R/W) and DVD.

While the inventive concept has been described with reference to exemplary embodiments, it will be apparent to those skilled in the art that various changes and modifications may be made without departing from the spirit and scope of the present inventive concept. Therefore, it should be understood that the above exemplary embodiments are not limiting, but illustrative.

What is claimed is:

1. A resuscitation training program generation system comprising:
    (a) at least one sensor configured to collect patient data; and
    (b) a database server in communication with the at least one sensor and comprising at least one microprocessor, wherein the at least one microprocessor is configured to execute:
        an acquisition section that acquires resuscitation event data on a cardiac arrest of a patient in an institution from the collected patient data and acquires resuscitation event data of other patients in the same institution from a resuscitation event data storage;
        an event categorization section that analyzes matrix data from a matrix data storage that comprises a taxonomy of etiologies of resuscitation, acquires a categorization of the cardiac arrest from one or more categories within the taxonomy of etiologies of resuscitation based on the matrix data, and creates an acquired categorization;
        an afferent data generator configured to read a plurality of afferent pathways based on the acquired categorization, combine the collected patient data with the resuscitation event data of other patients to form updated resuscitation event data, and create generated afferent data using the plurality of afferent pathways and the updated resuscitation event data;
        an efferent data generator configured to read a plurality of efferent pathways from an efferent category storage based on the acquired categorization to create generated efferent data, acquire training materials from a training materials storage based on the acquired categorization, and organize and modify the acquired training materials to address resuscitation roles and patient units in the institution; and
        generate a training program based on the generated efferent data, the generated afferent data, the updated resuscitation event data, and the organized and modified training materials.

2. The resuscitation training program generation system of claim 1, wherein the taxonomy of etiologies of resuscitation is arranged into a plurality of hierarchical levels, and the acquired categorization comprises categories from more than one of the plurality of hierarchical levels.

3. The resuscitation training program generation system of claim 1, wherein the efferent data generator further generates summary data specific to the patient and a summary response based on the summary data.

4. The resuscitation training program generation system of claim 3, wherein the case-specific response comprises one or more of structured debriefing, feedback data, a risk management response, or institutional response data.

5. The resuscitation training program generation system of claim 3, wherein the summary response comprises one or more of new policies, new procedures, new protocols, a launch of targeted initiatives, purchase a new equipment, implementation of new equipment, specific training, or institutional special projects.

6. The resuscitation training program generation system of claim 3, wherein the event categorization section acquires the categorization by transmitting graphical user interface (GUI) data for displaying the matrix data in a hierarchical series of windows to a workstation and receiving a selection of the acquired categorization using the GUI data from the workstation.

7. A method of generating a resuscitation training program, the method comprising:
    acquiring patient data using at least one sensor in communication with at least one microprocessor configured to detect and record the patient data, wherein the acquired patient data comprises resuscitation event data on a cardiac arrest of a patient in an institution;
    combining the acquired patient data with resuscitation data of other patients in the same institution to form updated resuscitation event data using the at least one microprocessor;
    providing a plurality of afferent pathways and efferent pathways to make up a resuscitation training continuous quality improvement (CQI) matrix based on the acquired patient data and the updated resuscitation event data, wherein the using the at least one microprocessor;
    hierarchically categorizing resuscitation events into one or more hierarchical categories within the resuscitation training CQI matrix using the at least one microprocessor;
    linking the one or more hierarchical categories of the resuscitation training CQI matrix with at least one of training materials, treatment algorithms, and special initiatives programs, using the at least one microprocessor; and
    organizing and modifying the at least one training materials, treatment algorithms, and special initiatives programs to generate the resuscitation training program using the at least one microprocessor.

8. The method of claim 7, wherein the plurality of afferent pathways comprise collected data associated with events leading up to an instance of a cardiopulmonary arrest.

9. The method of claim 7, wherein the plurality of efferent pathways comprise efferent pathways associated with reactions to data included within the CQI matrix.

10. The method of claim 9, wherein the reactions occur in response to one of a specific event including at least one of a debriefing event and dashboard feedback, and summary data including at least one of changes to training, new special initiatives programs, and modifications to the treatment algorithms.

11. The method of claim 7, wherein the step of hierarchically categorizing resuscitation events into one or more hierarchical categories within the resuscitation training CQI matrix comprises presenting a taxonomy for describing a plurality of etiologies of cardiopulmonary arrest.

12. The resuscitation training program generation system of claim 1, wherein the afferent data generator further reads general afferent pathways that are unrelated to the acquired categorization, and generates both related and general afferent data.

13. The resuscitation training program generation system of claim 1, further comprising a display in communication with the database server, wherein the efferent data generator controls the display in presenting the efferent data.

14. The resuscitation training program generation system of claim 4, wherein the training program is directed to the one or more of the structured debriefing, the feedback data, the risk management response, or the institutional response data of the case-specific response.

15. The resuscitation training program generation system of claim 5, wherein the training program is directed to the one or more of the new policies, the new procedures, the new protocols, the launch of targeted initiatives, the purchase of new equipment, the implementation of new equipment, the specific training, or the institutional special projects of the summary response.

* * * * *